(12) United States Patent
Wood

(10) Patent No.: US 6,331,280 B1
(45) Date of Patent: Dec. 18, 2001

(54) MEDICAL INSTRUMENT STERILIZATION SYSTEM

(75) Inventor: Timothy E. Wood, Weare, NH (US)

(73) Assignee: Poly Vac, Inc., Manchester, NH (US)

( * ) Notice: Subject to any disclaimer, the term of this patent is extended or adjusted under 35 U.S.C. 154(b) by 0 days.

(21) Appl. No.: 09/312,126

(22) Filed: May 14, 1999

(51) Int. Cl.[7] ................................................. A61L 2/00
(52) U.S. Cl. ........................ 422/300; 422/297; 422/300; 206/268; 206/269; 206/370; 206/438
(58) Field of Search ................................. 206/63.5, 368, 206/369, 370, 438; 422/300, 297

(56) References Cited

U.S. PATENT DOCUMENTS

| | | | |
|---|---|---|---|
| D. 332,664 | * 1/1993 | Sincock | D24/130 |
| 4,135,868 | 1/1979 | Schainholz | 422/310 |
| 4,627,542 | 12/1986 | Fredrickson | 211/150 |
| 4,643,303 | 2/1987 | Arp et al. | 206/363 |
| 4,798,292 | 1/1989 | Hauze | 206/439 |
| 4,959,199 | * 9/1990 | Brewer | 422/300 |
| 4,978,510 | * 12/1990 | Smith | 422/300 |
| 5,279,800 | 1/1994 | Berry, Jr. | 422/300 |
| 5,281,400 | 1/1994 | Berry, Jr. | 422/295 |
| 5,384,103 | 1/1995 | Miller | 422/310 |
| 5,424,048 | * 6/1995 | Riley | 422/300 |
| 5,441,707 | 8/1995 | Lewis et al. | 422/300 |
| 5,441,709 | * 8/1995 | Berry, Jr. | 422/300 |
| 5,492,671 | 2/1996 | Krafft | 422/26 |
| 5,573,741 | * 11/1996 | Riley | 422/300 |
| 5,599,512 | 2/1997 | Latulippe et al. | 422/300 |
| 5,827,487 | 10/1998 | Holmes | 422/297 |
| 5,882,612 | 3/1999 | Riley | 422/300 |

FOREIGN PATENT DOCUMENTS 295 03 691
U1 8/1995 (DE) ............................. B65B/55/24

* cited by examiner

Primary Examiner—Terrence R. Till
Assistant Examiner—Imad Soubra
(74) Attorney, Agent, or Firm—Hayes, Soloway, Hennessey, Grossman & Hage, P.C.

(57) ABSTRACT

A medical instrument sterilization system includes a sterilization tray having a bottom wall and an array of ventilation/mounting holes in the bottom wall. The ventilation/mounting holes are arranged evenly spaced at least in part in the bottom wall. Preferably the ventilation/mounting holes comprise a central portion and one or more lobes. In a particularly preferred embodiment, the ventilation/mounting holes comprise a plurality of like cruciform-shaped holes. Completing the invention are one or more rigid brackets having posts arranged to project through the ventilation/mounting holes for anchoring at selected positions on the tray.

30 Claims, 12 Drawing Sheets

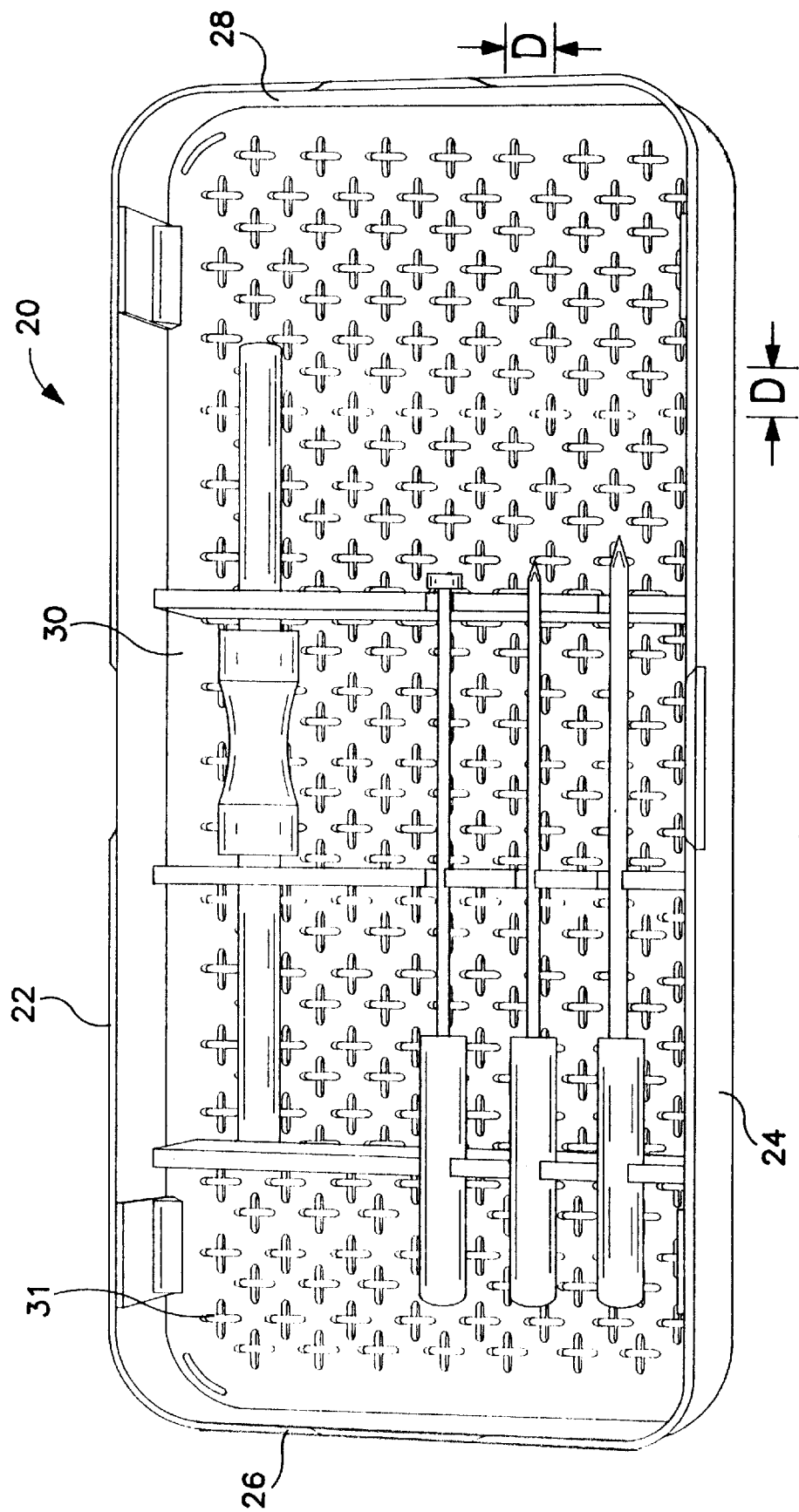

MEDICAL INSTRUMENT STERILIZATION SYSTEM

FIELD OF THE INVENTION

This invention relates to the field of sterilization of surgical instruments. More particularly, the invention relates to an improved system for securing surgical instruments at fixed positions in sterilization trays.

BACKGROUND OF THE INVENTION

Surgical instruments are often transported in trays prior to use. The instruments are usually laid out in a certain way in the tray and subjected to sterilization in a steam autoclave or similar sterilization apparatus. In order to maintain separations between the various instruments in the tray, the instruments are supported or retained by brackets, clips, posts or other fixation devices positioned in the tray. Following sterilization, the tray full of instruments is transported to an operating room and placed close to the surgical team whose members withdraw the instruments from the tray as needed for a particular surgical procedure. Many times, the instruments are selectively arranged in the tray so that they can be picked from the tray in the general order that they are needed for the particular procedure. Examples of such trays are found in U.S. Pat. Nos. 4,643,303; 5,424,048 and 5,492,671.

As seen from the above patents, the known devices for organizing and fixating medical instruments in a tray include various types of brackets, clips and posts which project up from the bottom of the tray, the instruments being held in place within slots and clip openings and/or between the posts. A plurality of such fixation devices are spaced running parallel or perpendicular to each other in the tray so that they engage and support the opposite sides or ends of various different length instruments.

Most prior art fixation devices are able to effectively locate and hold instruments which are more or less straight and regularly shaped. However, they are not particularly suitable for fixating oddly or irregularly shaped instruments such as retractors and other longer instruments that have, e.g. ring handles. This is because there is insufficient flexibility in the placement of the various fixation devices within the tray as to enable the devices to closely engage the instruments while still organizing the instruments in an efficient layout within the tray. This results from the fact that the fixation devices often are plugged into the ventilation holes usually present in the bottom of the tray such that a fixation device only can be placed where there are holes in the bottom of the tray.

As the number of such holes is limited by manufacturing cost, required tray bottom strength and the need to prevent the instruments from projecting through the holes, so also are the positions of the various fixation devices. Consequently, either the tray contains too few properly fixated instruments or a larger number of instruments some of which may not be properly fixated. Thus, if the tray is shaken or tilted, instruments may become disengaged from the fixation devices and assume skewed positions in the tray so that they may become damaged and difficult to remove without upsetting other instruments in the tray. In extreme cases, loose instruments may even fall out of the tray and become contaminated. Since a tray may contain a complete set of instruments needed for a particular surgical procedure, this may require that another full tray of sterilized instruments be made available to the surgical team.

Another consideration is that the instruments required to perform a specific surgical procedure may vary greatly between hospitals and even surgical teams within specific hospitals. Therefore, it is practically impossible to design a standard tray configuration that will be acceptable for all hospitals and surgical teams. Thus, an optimum instrument fixation arrangement is one which is enormously flexible so that it can be customized to each individual hospital and surgical team, because the numbers and types of instruments being presented in the trays change constantly.

In order to overcome the aforesaid problems of the prior art, there is proposed in U.S. Pat. No. 5,827,487 a surgical instrument fixation device for use in a sterilization tray, comprising a rail of optional length and having at least two pegs projecting from the underside of the rail which are sized and spaced apart so as to be able to plug into at least two of the ventilation holes in the bottom wall of the tray. As disclosed in the aforesaid U.S. Pat. No. 5,827,487, the ventilation holes are usually arranged in a rectangular array of columns and rows so that a rail can be positioned at any location within a column or row, i.e. running parallel or perpendicular. Typically, the rails are releasably fixed in position by threaded fasteners driven from the underside of the tray.

However, since surgical instruments come in a wide variety of shapes and forms, it is impractical to have a single rail type fixation device for all types of surgical instruments. Thus, the art has developed various systems wherein supports and dividers for the surgical instruments are provided in modular or kit form for selective positioning within the tray, for example, by plugging selected support elements through holes in a portion of the tray and fixing the element in place. The support elements can thus be arranged to match the shape of the surgical instrument to be sterilized.

Examples of such products are shown in U.S. Pat. No. 4,135,868 to Sheinholz and U.S. Pat. No. 5,384,103 to Miler. Similar products are commercially available from companies such as Poly-Vac, Incorporated of Manchester, N.H. and other suppliers. Some of these prior devices include integrally molded stubs, for example positioned on the bottom of the flexible inserts, which stubs can be locked into the ventilation holes in the tray as shown, for example, in FIG. 1 of Miller U.S. Pat. No. 5,384,103. They may also comprise separate, rigid holding elements such as shown in FIG. 3 of the above '103 patent where a rigid holder for the support element is fastened by threaded fasteners to the tray or to a shelf carried by the tray. In the '868 patent, the support element for a soft sponge rubber, constituting a hold down pad, is supported by a channel member having outwardly extending buttons which can be forced into ventilation holes in the cover or base of the sterilizing tray. Another prior U.S. patent, U.S. Pat. No. 4,798,292 shows hollow pegs having elongated legs which are used for attachment to a perforated sterilizer tray.

While all of the systems described in the prior patents and commercially available products provide a certain amount of flexibility, they do not provide both strong security for the support members and low cost. Nor do they allow for ease of removal of a securely mounted support so that the supports can be differently positioned in the sterilization trays for holding different shapes of surgical instruments to be sterilized.

In order to address this latter problem, there is described in U.S. Pat. No. 5,599,512 a commercially available (from Poly Vac, Inc., of Manchester, N.H.) sterilization support element provided with sets of resiliently deformable bayonet type fingers for locking the support elements in position in ventilation holes in bottom wall of a sterilization tray. The support elements are simply and easily removed and repositioned in the tray by means of a simple tool which engages the ends of the bayonet fingers, and pushes them back through the holes.

While all of the systems described in the above prior patents, and in commercially available products provide a certain amount of flexibility, they all have disadvantages. They all require tools for assemblying and/or removing the supports or dividers. Also, those prior art systems employing threaded fasteners, locking rings or the like, require extra parts counts. Additionally, since the mounting holes are arranged in parallel rows, standard fixation devices and separators are limited to parallel and/or perpendicular positioning relative to one another.

SUMMARY OF THE INVENTION

It is thus an objection of the present invention to overcome the aforesaid and other disadvantages of the prior art.

More particularly, in accordance with the present invention, a sterilization tray in which the bottom wall of a sterilization tray is populated at least in part with evenly spaced ventilation/mounting holes. Preferably the ventilation/mounting holes comprise a central hole and one or more lobes. In a particularly preferred embodiment, the ventilation/mounting holes comprise a plurality of like cruciform-shaped holes. Completing the invention are one or more brackets having posts arranged to project through the ventilation/mounting holes for anchoring at selected positions on the tray.

BRIEF DESCRIPTION OF THE DRAWINGS

Yet other objects and advantages of the present invention will be apparent in the following detailed description of the invention, taken in conjunction with the accompanying drawings wherein like numerals depict like parts, and wherein:

FIG. 1 is a top view of a sterilization tray system made in accordance with the present invention;

DETAILED DESCRIPTION OF THE INVENTION

Figure 1A:
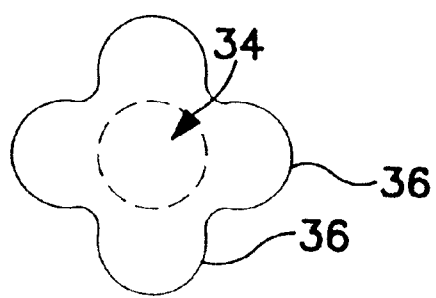
FIGS. 1a, 1b, 1c and 1d are enlarged top plan views showing details of mounting/ventilation holes in accordance with the present invention.
Figure 1B:
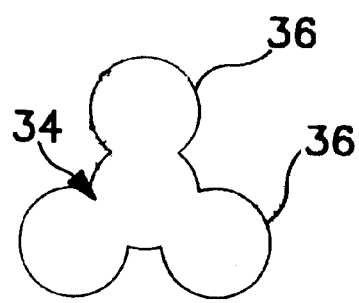
Figure 1C:
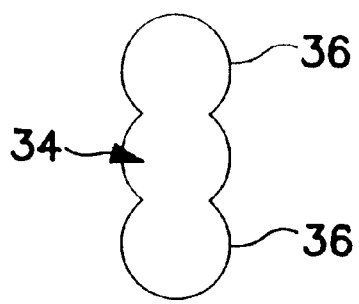
Figure 1D:
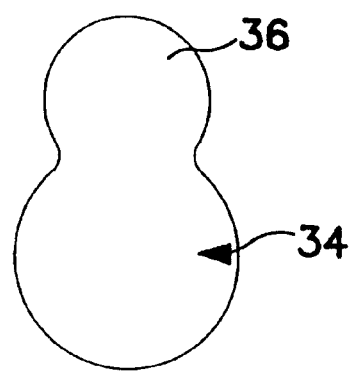
Figure 2:
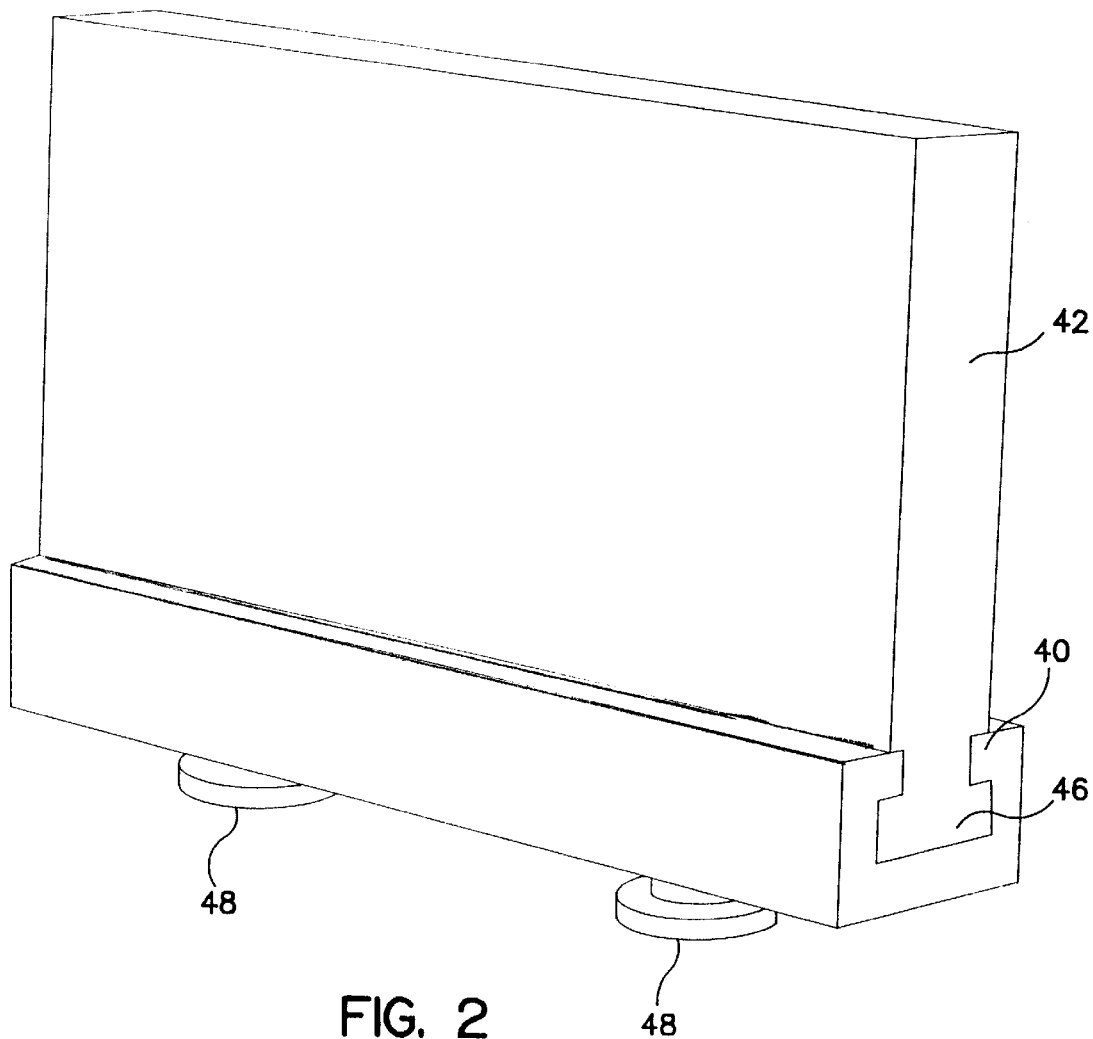
FIG. 2 is an enlarged perspective view of one form of bracket portion of the present invention.
Figure 3:
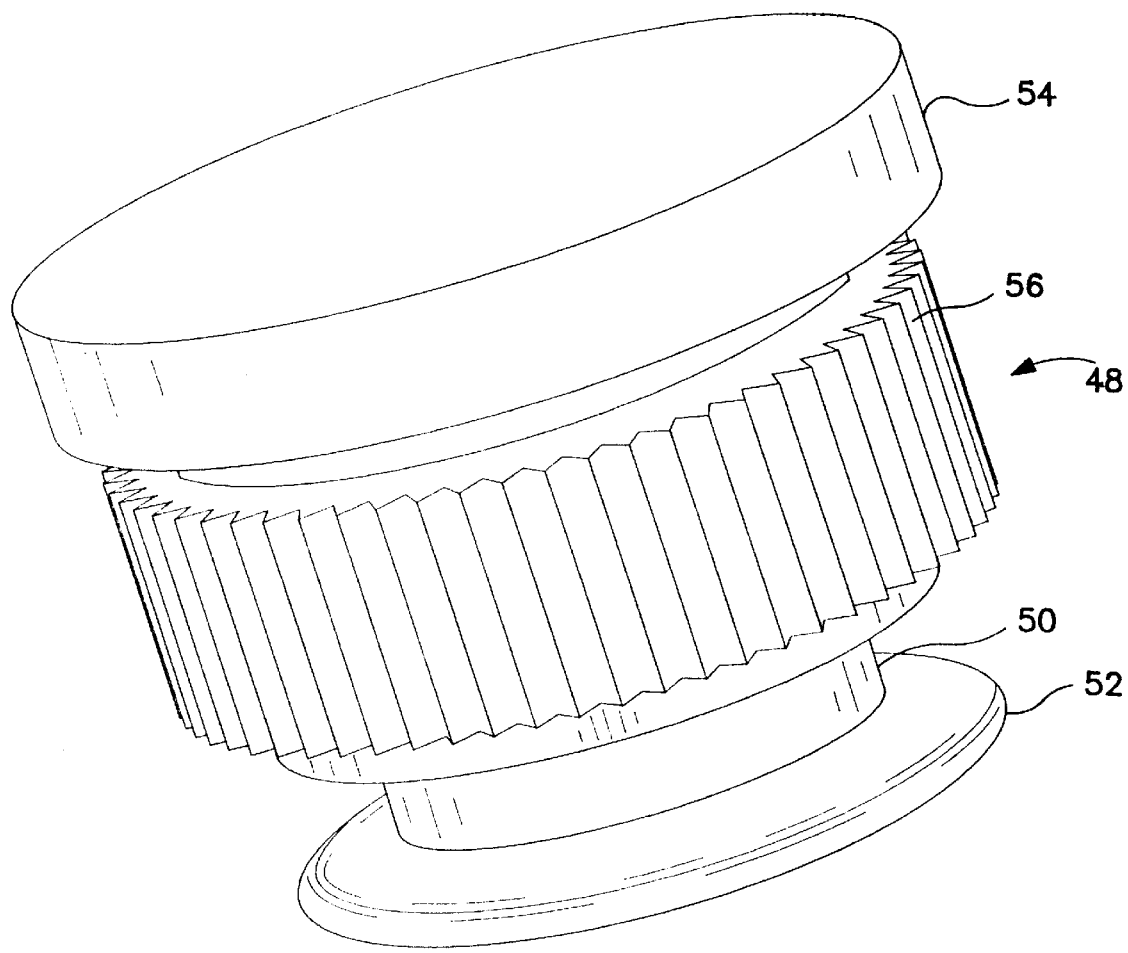
FIG. 3 is an enlarged, perspective view of a mounting post portion of a bracket of the present invention.

Referring now to FIGS. 1–3, the sterilization tray system in accordance with the present invention comprises a rigid, rectangularly shaped tray 20 having a pair of side walls 22, 24, a pair of end walls 26, 28, and a bottom wall 30 defining a generally rectangular interior space. Preferably tray 20 is provided with integral feet 32 so that the tray bottom wall 30 is spaced above the surface upon which it is placed.

Formed in the tray bottom wall 30 are a plurality of holes 32. Holes 32 are evenly spaced from one another by an on center distance D in a plurality of vertical, horizontal and diagonal columns. Holes 32 serve the dual purpose of permitting ingress or egress of steam or other sterilant to circulate through the tray, and also serve for locating instrument brackets or dividers as will be described in detail hereinafter, interiorly of the tray. In a preferred embodiment of the invention, holes 32 are formed in a cruciform shaped pattern having a central portion 34 and four evenly spaced lobes 36 (see FIG. 1a). However, the holes 32 may comprise a center portion 34 and three lobes 36 (see FIG. 1b), or a central portion 34 and two lobes 36 (FIG. 1c). In yet another embodiment of the invention, hole 32 comprises a dumbbell shaped hole consisting of a large and a small lobe 36a, 36b, respectively.

The sterilization tray system in accordance with the present invention also includes one or more support brackets 40 in which are mounted instrument dividers 42, or instrument damps 44 or the like. Referring in particular to FIGS. 2 and 3, bracket 42 comprises an elongated rail having a T-shaped channel 46 in which a selected divider 42 or instrument clamp 44 is slidably mounted. Each bracket 40, which may be formed of a rigid plastic or the like, is anchored in selected locations in holes 32 to the bottom wall 30 of the tray by means of posts 48 which extend through stepped holes 50 in brackets 40, and project from the bottom of the bracket. Each post 48 has a reduced diameter neck or groove 50 and a flange 52 formed at the distal end thereof, and an enlarged head 54 and a knurled body portion 56 for press-fitting into stepped holes 50 in bracket 40. Reduced diameter neck 50 has a length approximating that of the thickness of tray bottom wall 30.

Posts 48 are spaced apart by a distance equal to twice the distance between holes 32. Also, flange portions 52 are sized to fit through central portion 34 of holes 32 (shown in dotted lines), but are oversized relative to the node portions 36. Thus, posts 48 may be loaded into holes or removed from holes 32 by the center portions. However, the brackets 40 may then be locked in place by sliding the brackets with their associated posts into the nodes 36.

A feature and advantage of the present invention is the ability to universally mount dividers and brackets at essentially any location on the tray. Thus, by providing holes 32 evenly spaced across the tray bottom wall, brackets 40 may be mounted at any location running in a horizontal, vertical or diagonal direction. Moreover, no special tools are needed for mounting and unmounting the brackets, it being a simple matter to locate the brackets in the desired holes, and then slide the brackets from central locations in the holes into a corresponding node position whereupon the pins and associated brackets will become friction held in position on the tray.

Figure 4:
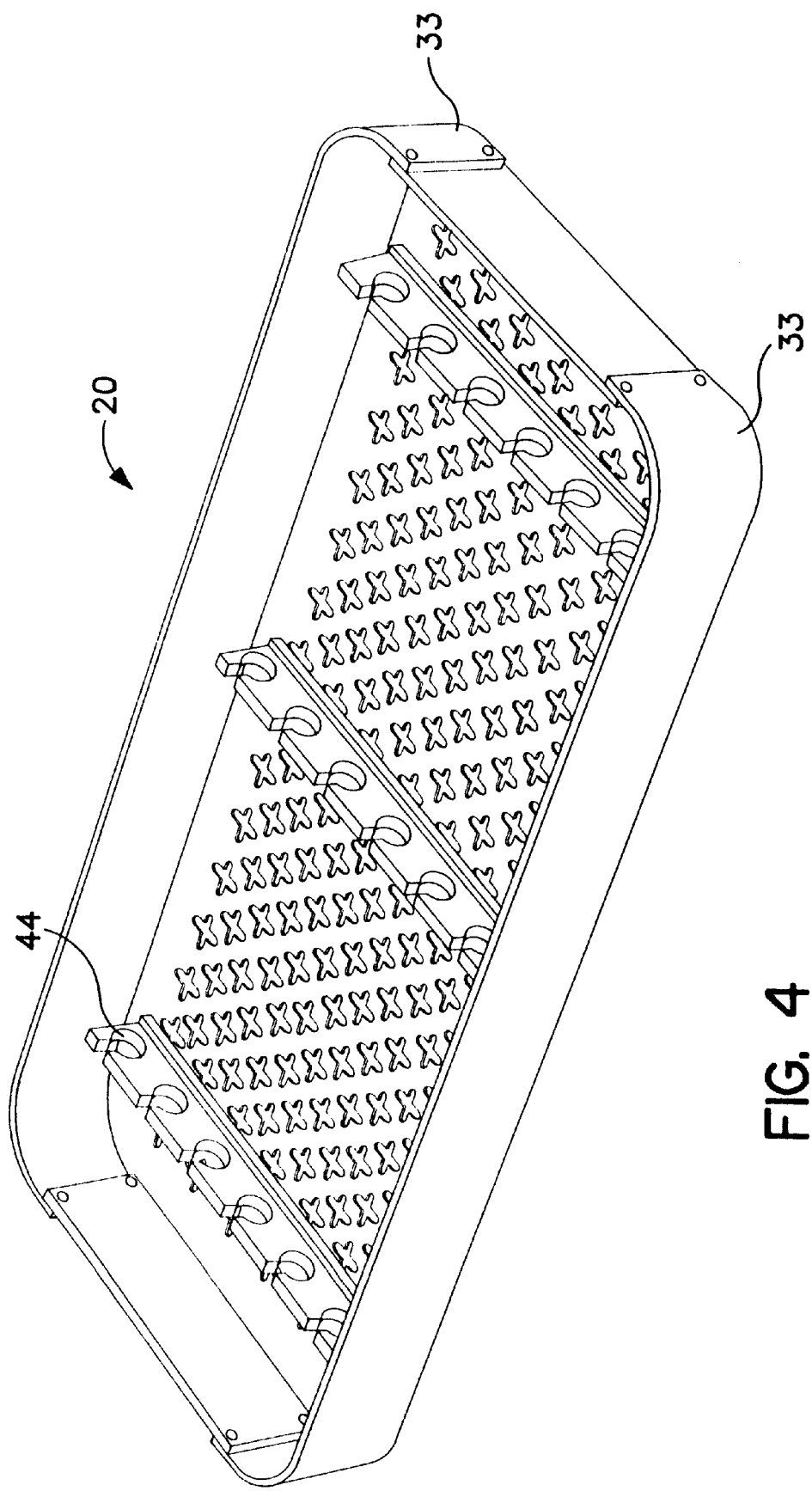
FIGS. 4, 5 and 6 show alternative embodiments of sterilization trays made in accordance with the present invention.
Figure 5:
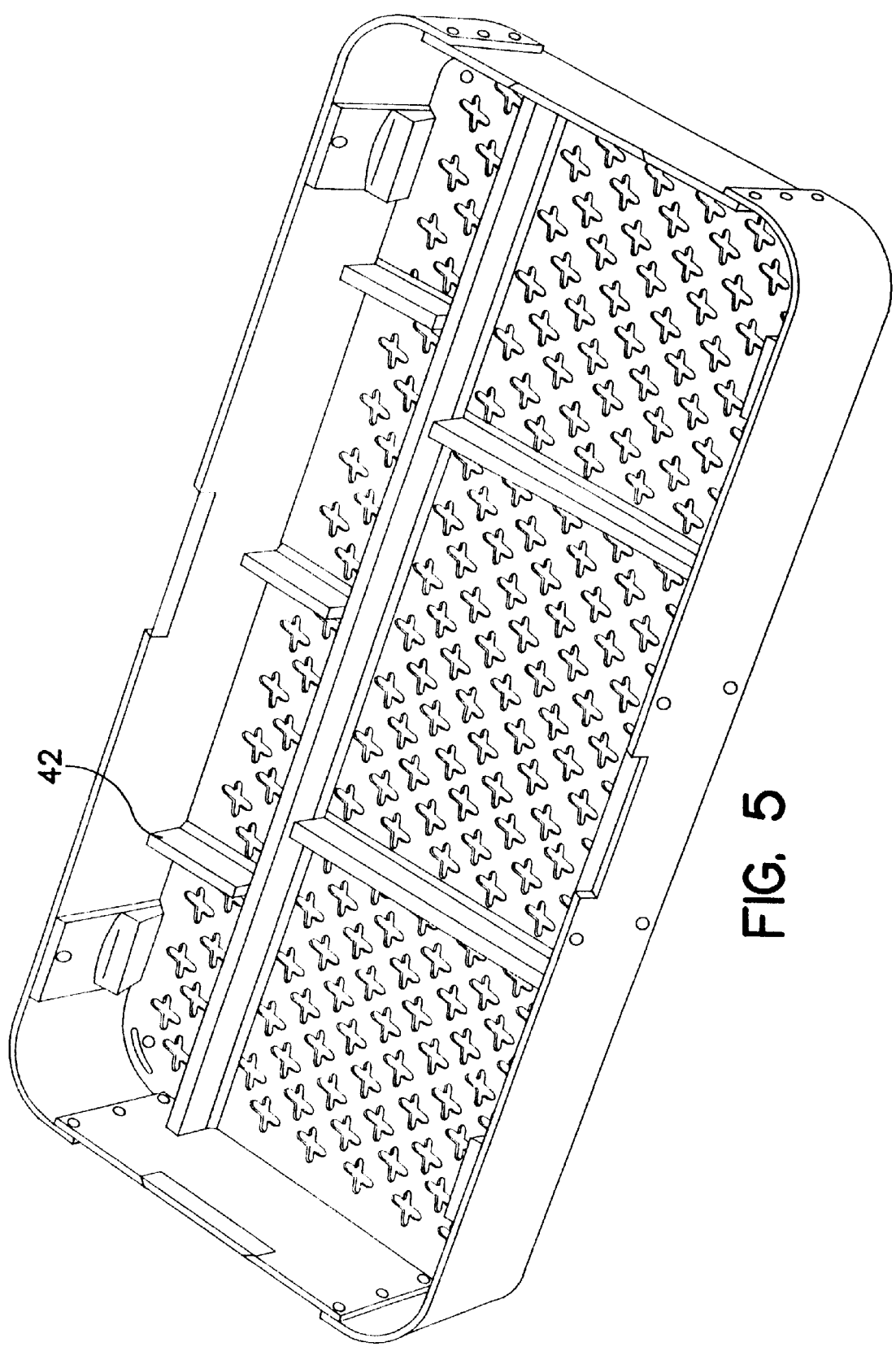
Figure 6:
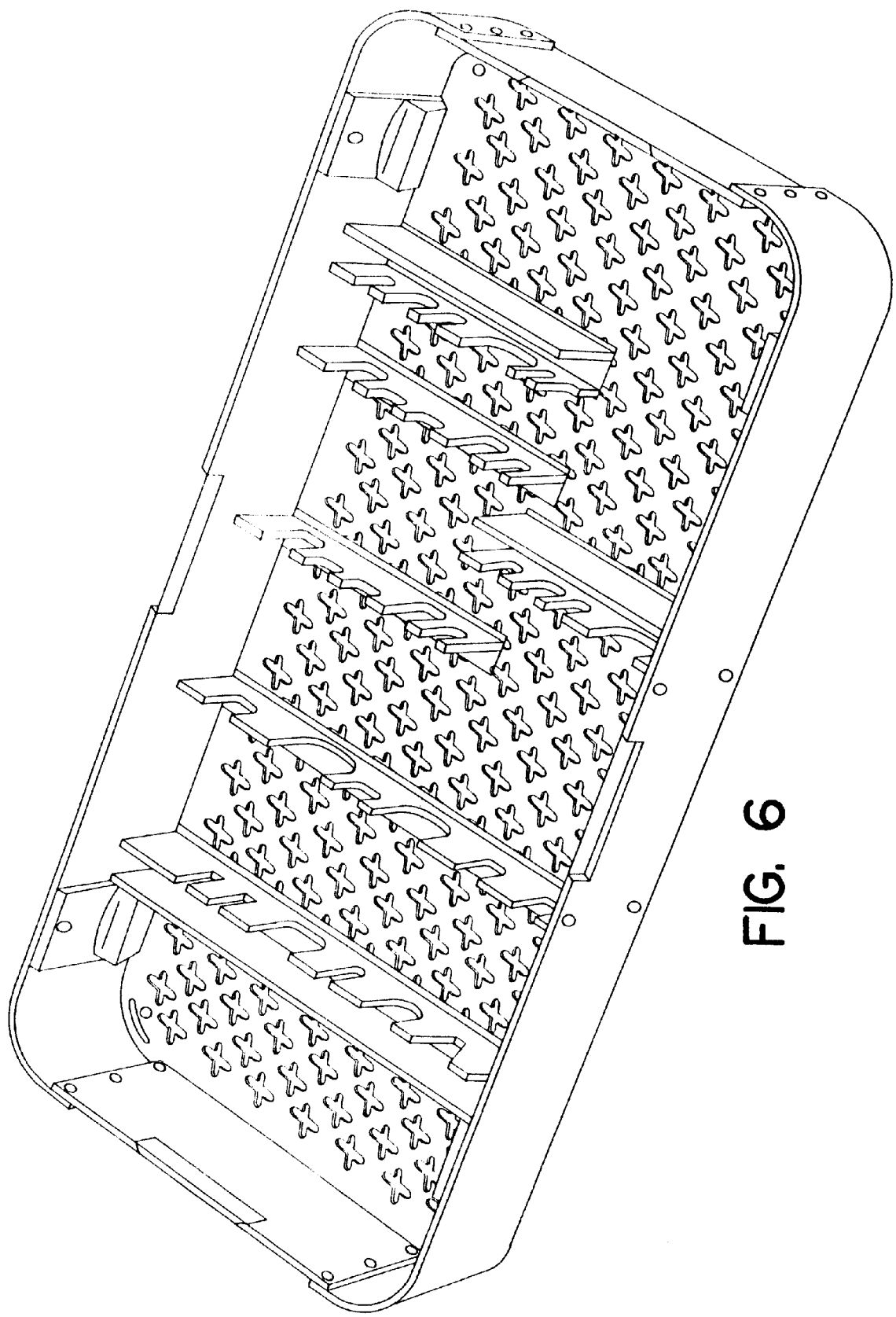
Figure 7:
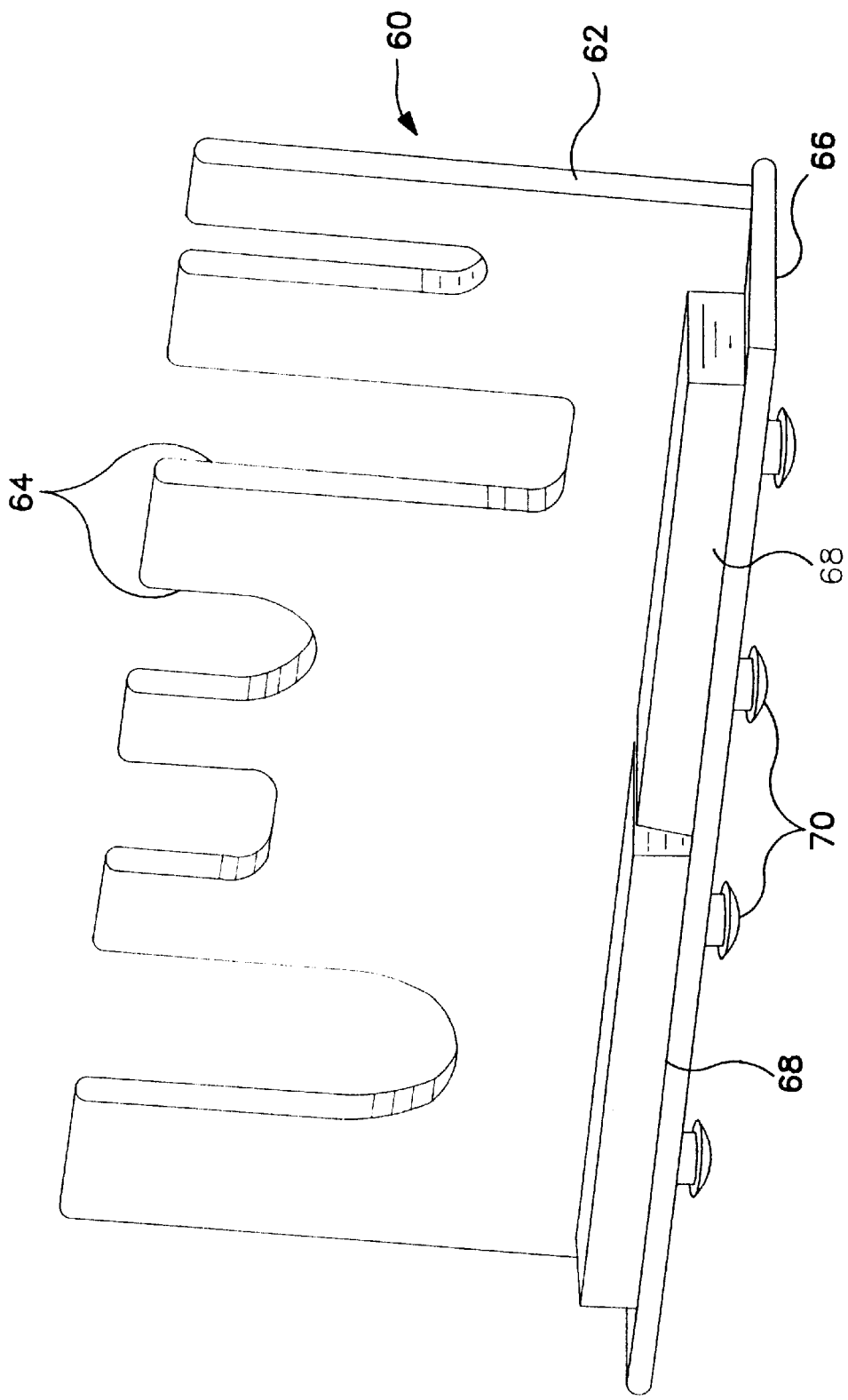
FIG. 7 is a view similar to FIG. 2 showing another embodiment of fastening bracket made in accordance with the present invention.

Referring to FIGS. 4 and 5, in a preferred embodiment of the invention, brackets 40 comprise short stub brackets each having a pair of posts 48 extending therethrough. Of course, the brackets can be made longer, and have three or more spaced posts. However, an advantage of the present invention is that it permits the sterilization tray system to be manufactured, packaged and used as a kit of parts. Thus, a plurality of brackets 40 may be packaged together with a variety of dividers or slotted instrument clamps, etc., which may be made of, for example, silicone rubber. Silicone rubber is relatively easily cut. Thus, the user could purchase elongated strips or rolls of silicone rubber strips, cut them to desired length, and thus customize a tray in the field.

Figure 8:
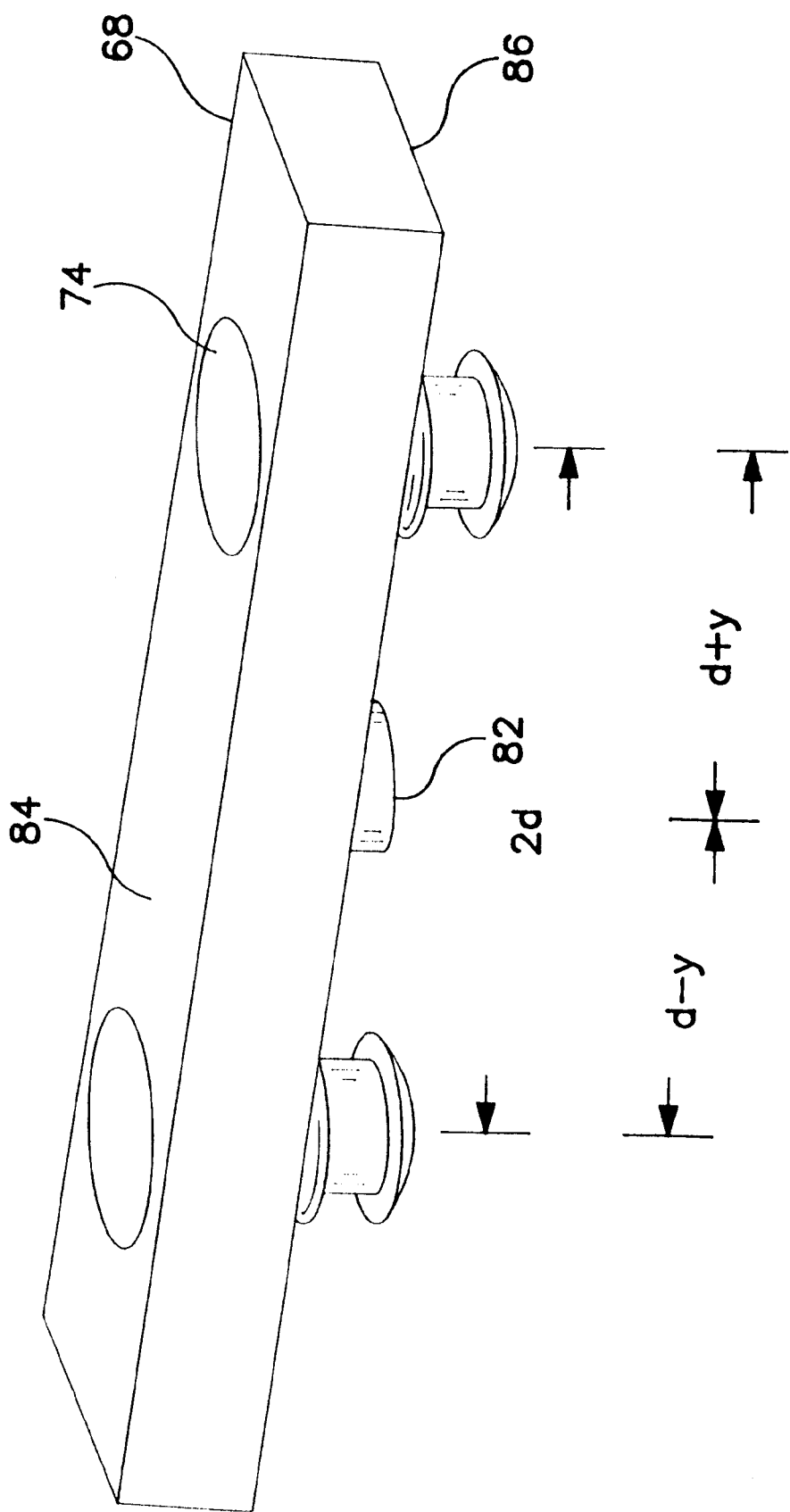
FIG. 8 is an enlarged perspective view of an alternative fastening bracket in accordance with the present invention.
Figure 9:
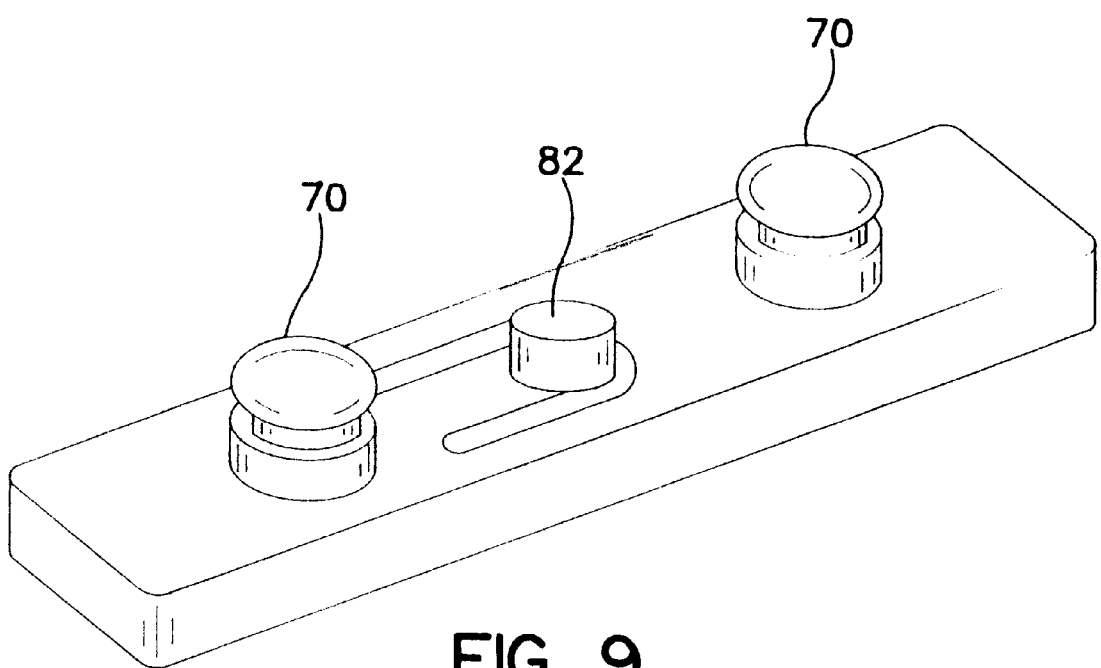
FIG. 9 is a view similar to FIG. 8, but taken from the bottom.
Figure 10:
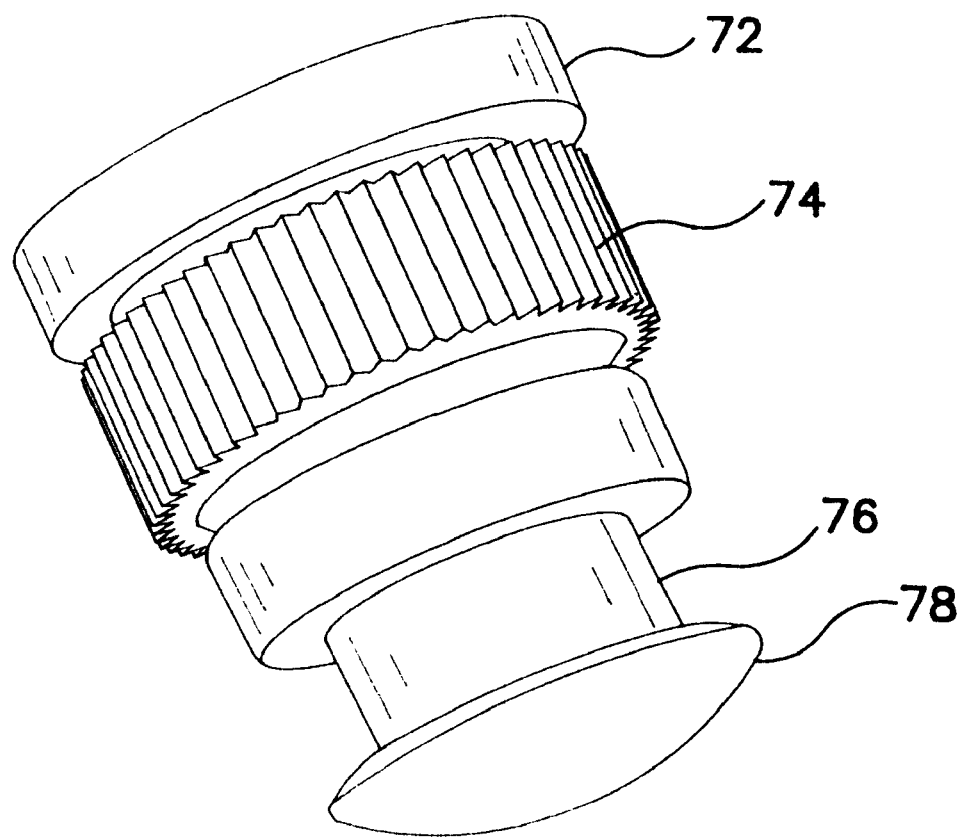
FIG. 10 is an enlarged view showing details of the post portion of the bracket of FIG. 7.

FIGS. 6–11 illustrate alternative forms of posts, brackets, dividers, and instrument supports in accordance with the present invention. Referring in particular to FIGS. 7–10, the instrument dividers/supports comprise generally L-shaped members 60 formed of silicone rubber or the like, and comprising a upright wall 62 in which may be provided one or more slots 64 for accommodating a surgical instrument (not shown) and a short base wall 66. Wall 66 is sandwiched between locking brackets 68, as will be described in detail hereinafter and the tray bottom wall 30, by means of posts 70 which extend through holes (not seen) in walls 66 and walls 32 in the tray bottom wall 30. Referring in particular to FIGS. 8, 9 and 10, post 70 which include an enlarged head 72 are mounted in holes 74 formed in bracket 68 and are friction held in place therein by knarled section 74. Each post also includes a reduced diameter neck 76 adjacent its distal end, inbound of a flared section 78. As before, posts 70 preferably are spaced apart a distance equal to twice the spacing D.

Referring in particular to FIGS. 8 and 9, in a preferred embodiment of the invention bracket 64 includes a locking post 82 which is carried on a resiliently deformable arm 84. Locking post 82 normally extends below the lower surface 86 of bracket 68, and is located between posts 70, offset from the midpoint therebetween by a distance "Y" which equals the distance between hole central portions 34 and nodes 36. Thus, when brackets 68 are loaded in holes 32, and slid into a node position, locking post 82 snaps down locking the bracket in position. However, it is a simple matter to remove bracket 68 by pressing post 82 upwards, and then sliding the bracket back to central position.

Figure 11:
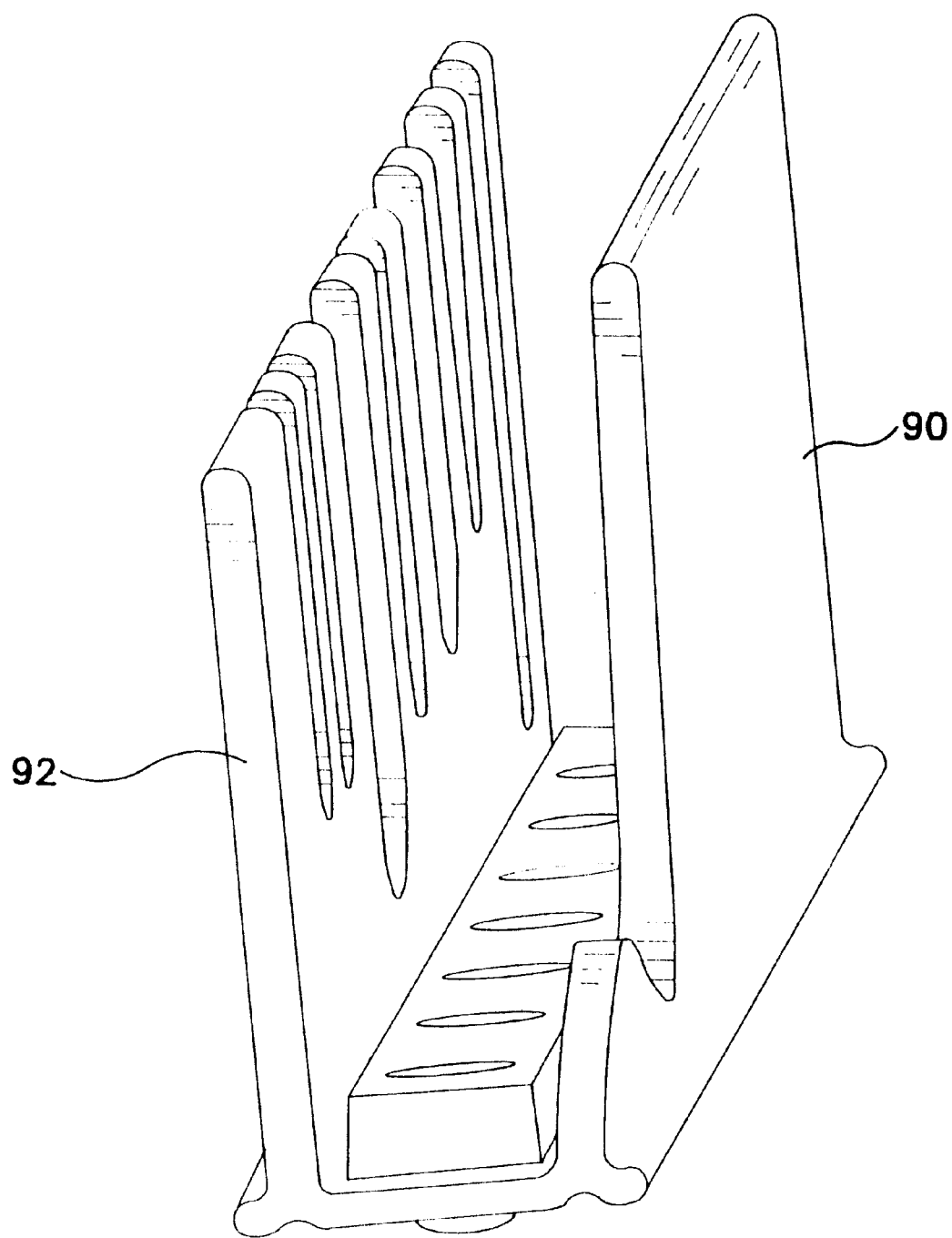
FIG. 11 is an enlarged view, similar to FIG. 7 and showing another alternative embodiment of fastening bracket in accordance with the present invention.

Various changes may be made in the invention without departing from the spirit and scope thereof. For example, as shown in FIG. 11, the instrument support may comprise a generally U-shaped member having a solid divider wall 90 and a slotted wall 92. Yet other changes may be made without departing from the spirit and scope of the invention.

What is claimed is:

1. In a combination including a sterilization tray assembly for sterilizing surgical instruments, said assembly including a tray having a plurality of holes and upstanding elements removably mounted on said tray for clasping or separating surgical instruments on said tray, wherein the bottom wall of said tray is populated at least in part with evenly spaced ventilation/mounting holes, wherein each of which ventilation/mounting holes comprise a central portion having at least one lobe communicating therewith, wherein each upstanding element has integrally formed mounting posts depending from the lower surface thereof, each post having a reduced diameter neck and a flange formed at a distal end thereof, the reduced diameter neck having a length approximating that of the thickness of the bottom wall of the tray, and the post flange portions are sized to fit through the holes' central portions, but are oversized relative to the hole lobes.

2. The combination of claim 1, wherein each of the ventilation/mounting holes are identically sized and spaced.

3. The combination of claim 1, wherein the ventilation/mounting holes each comprise a central portion having two lobes communicating therewith.

4. The combination of claim 1, wherein the ventilation/mounting holes each comprise a central portion having three lobes communicating therewith.

5. The combination of claim 1, wherein the ventilation/mounting holes each comprise a central portion having four lobes communicating therewith.

6. The combination of claim 1, wherein said ventilation/mounting holes are cruciform-shaped.

7. The combination of claim 1, wherein the ventilation/mounting holes are evenly spaced from one another in rows, columns, and diagonals.

8. The combination of claim 1, wherein said upstanding element comprises a resiliently deformable material.

9. The combination of claim 8, wherein said resiliently deformable material comprises silicone rubber.

10. The combination of claim 1, wherein said upstanding element comprises a generally L-shaped elongate member.

11. The combination of claim 1, wherein said upstanding element comprises a generally U-shaped elongate member.

12. The combination of claim 1, wherein said upstanding element comprises a generally U-shaped elongate member, wherein one leg of the U comprises a solid wall, while the other leg has one or more slots formed therein.

13. The combination of claim 1, wherein said upstanding element comprises a solid wall.

14. The combination of claim 1, wherein said upstanding element includes at least one slot formed therein.

15. In a combination including a sterilization tray assembly for sterilizing surgical instruments, said assembly including a tray having a plurality of holes and upstanding elements mounted in a relatively rigid support element which in turn is removably mounted on said tray, clasping or separating surgical instruments on said tray, wherein the bottom wall of said tray is populated at least in part with evenly spaced ventilation/mounting holes, wherein each of which ventilation/mounting holes comprise a central portion having at least one lobe communicating therewith, wherein each relatively rigid support element has integrally formed mounting posts depending from the lower surface thereof, each post having a reduced diameter neck and a flange formed at a distal end thereof, the reduced diameter neck having a length approximating that of the thickness of the bottom wall of the tray, and the post flange portions are sized to fit through the holes' central portions, but are oversized relative to the hole lobes.

16. The combination of claim 15, wherein each of the ventilation/mounting holes are identically sized and spaced.

17. The combination of claim 15, wherein the ventilation/mounting holes each comprise a central portion having two lobes communicating therewith.

18. The combination of claim 15, wherein the ventilation/mounting holes each comprise a central portion having three lobes communicating therewith.

19. The combination of claim 15, wherein the ventilation/mounting holes each comprise a central portion having four lobes communicating therewith.

20. The combination of claim 15, wherein said ventilation/mounting holes are cruciform-shaped.

21. The combination of claim 15, wherein the ventilation/mounting holes are evenly spaced from one another in rows, columns, and diagonals.

22. The combination of 15, wherein said relatively rigid support element comprises an elongated rail having a T-shaped channel in which is slidably mounted said upstanding element.

23. The combination of claim 15, and further comprising a locking post extending below the lower surface of the rigid support element, between said mounting posts, said locking post being located offset from the midpoint between said mounting posts by a distance equal to the distance between the hole central portions and the nodes.

24. The combination of claim 15, wherein said upstanding element comprises a resiliently deformable material.

25. The combination of claim 24, wherein said resiliently deformable material comprises silicone rubber.

26. The combination of claim 15, wherein said upstanding element comprises a generally L-shaped elongate member.

27. The combination of claim 15, wherein said upstanding element comprises a generally U-shaped elongate member.

28. The combination of claim 15, wherein said upstanding element comprises a generally U-shaped elongate member, wherein one leg of the U comprises a solid wall, while the other leg has one or more slots formed therein.

29. The combination of claim 15, wherein said upstanding element comprises a solid wall.

30. The combination of claim 15, wherein said upstanding element includes at least one slot formed therein.

* * * * *